United States Patent
Boone et al.

(12)

(10) Patent No.: US 11,631,549 B2
(45) Date of Patent: Apr. 18, 2023

(54) ELECTRICAL COMPONENT AND METHOD OF FORMING SAME

(71) Applicant: Medtronic, Inc., Minneapolis, MN (US)

(72) Inventors: Mark R. Boone, Gilbert, AZ (US); Joachim Hossick-Schott, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/367,828

(22) Filed: Jul. 6, 2021

(65) Prior Publication Data

US 2022/0037091 A1 Feb. 3, 2022

Related U.S. Application Data

(60) Provisional application No. 63/058,901, filed on Jul. 30, 2020.

(51) Int. Cl.
| | | |
|---|---|---|
| *H01G 9/048* | (2006.01) | |
| *H01G 9/15* | (2006.01) | |
| *H01G 9/08* | (2006.01) | |
| *H01G 9/07* | (2006.01) | |

(52) U.S. Cl.
CPC .............. *H01G 9/048* (2013.01); *H01G 9/08* (2013.01); *H01G 9/15* (2013.01); *H01G 9/07* (2013.01)

(58) Field of Classification Search
CPC ....................................................... H01G 9/15
See application file for complete search history.

(56) References Cited

U.S. PATENT DOCUMENTS

| | | | |
|---|---|---|---|
| 5,812,366 A | * | 9/1998 | Kuriyama ................ H01G 9/15 361/523 |
| 6,510,044 B1 | | 1/2003 | Loeffelholz et al. |
| 8,199,461 B2 | | 6/2012 | Zednicek et al. |
| 8,992,635 B2 | | 3/2015 | Otterstedt |
| 2003/0218859 A1 | | 11/2003 | Yoshida |
| 2005/0280978 A1 | | 12/2005 | Sakaguchi et al. |
| 2010/0020473 A1 | | 1/2010 | Prymak et al. |
| 2012/0300369 A1 | | 11/2012 | Lee et al. |
| 2016/0284476 A1 | * | 9/2016 | Paulus ................... H01G 9/052 |
| 2017/0172505 A1 | | 6/2017 | Ruben et al. |
| 2020/0154567 A1 | | 5/2020 | Kim et al. |

FOREIGN PATENT DOCUMENTS

JP 2000114113 4/2000

* cited by examiner

*Primary Examiner* — Eric W Thomas
(74) *Attorney, Agent, or Firm* — Mueting Raasch Group

(57) ABSTRACT

Various embodiments of an electrical component and a method of forming such component are disclosed. The electrical component includes a substrate having a first major surface, a second major surface, an alloy layer disposed on the first major surface of a substrate, and tantalum material disposed on the alloy layer such that the alloy layer is between the tantalum material and the first major surface of the substrate. The tantalum material includes bonded tantalum particles. The electrical component can also include a dielectric layer disposed on the tantalum particles, a cathode electrode disposed over the tantalum material, and an anode electrode disposed on the second major surface of the substrate.

11 Claims, 3 Drawing Sheets

ELECTRICAL COMPONENT AND METHOD OF FORMING SAME

This application claims the benefit of U.S. Provisional Patent Application Ser. No. 63/058,901, filed on Jul. 30, 2020, which is incorporated by reference herein in its entirety.

TECHNICAL FIELD

This disclosure generally relates to electrical components. In particular, this disclosure relates to electrical components suitable for use in implantable devices.

BACKGROUND

A wide variety of electronic assemblies such as those that are utilized for implantable medical devices (IMDs) employ electronic circuitry, e.g., for providing electrical stimulation of body tissue and/or monitoring a physiologic condition. Such IMDs can deliver electrical therapy energy in the form of shocking energy and stimulating pulses to selected body tissue and typically include output circuitry for providing the electrical energy under prescribed conditions and at least one lead bearing a stimulation electrode for delivering the electrical energy to the selected tissue. For example, cardiac pacemakers and implantable cardioverter-defibrillators (ICDs) have been developed for maintaining a desired heart rate during episodes of bradycardia or for applying cardioversion or defibrillation therapies to the heart upon detection of serious arrhythmias. Other nerve, brain, muscle, and organ tissue stimulating medical devices are also known for treating a variety of conditions.

Currently available IMDs, including ICDs and implantable pulse generators (IPGs), are typically formed having a metallic housing that is hermetically sealed and, therefore, is impervious to body fluids, and a header or connector assembly mounted to the housing for making electrical and mechanical connection with one or more leads. Such devices also possess telemetry capabilities for communicating with external devices. Over the past 20 years, IMDs have evolved from relatively bulky devices to complex miniaturized devices that exhibit increasing functionality. For example, numerous improvements have been made in cardioversion/defibrillation leads and electrodes that have enabled the cardioversion/defibrillation energy to be precisely delivered to selected one or more portions of upper and lower heart chambers. The high voltage output circuitry has also been improved in many respects to provide monophasic, biphasic, or multi-phase cardioversion/defibrillation shock or pulse waveforms that are efficacious, sometimes with particular combinations of cardioversion/defibrillation electrodes.

The miniaturization of IMDs is driving size and cost reduction of all IMD components, including the electronic circuitry components, where it is desirable to increase the density and reduce the size of such components so that the overall circuitry can be more compact. As the dimensions of IMDs decrease, the electronic circuits of the IMDs are formed as integrated circuits to fit within a minimal space. Furthermore, as the dimensions of the components are also being reduced, it is desirable to improve the use of the available space within the IMD package.

Electronic circuitry for IMDs and other electronic devices can include one or more capacitors. Such capacitors are passive components that store potential energy in an electric field and are designed to add capacitance to circuits. Various types of capacitors can be utilized, including ceramic and electrolytic capacitors. Tantalum capacitors are a type of electrolytic capacitor that have a relatively high capacitance density compared to other capacitors such as ceramic capacitors.

SUMMARY

The techniques of this disclosure generally relate to electrical components and methods for forming such electrical components. In one or more embodiments, an electrical component can include an alloy layer disposed on a first major surface of a substrate. Tantalum material can be disposed on the alloy layer, where the tantalum material can include tantalum particles. The electrical component can include a dielectric disposed on the tantalum particles. The electrical component can include a cathode electrode disposed over the tantalum material and an anode electrode disposed on a second major surface of the substrate. In one or more embodiments, the electrical component can form a capacitor that can be utilized in any suitable electronic circuit or device.

In one example, aspects of this disclosure relate to an electrical component that includes a substrate having a first major surface and a second major surface. The electrical component also includes an alloy layer disposed on the first major surface of the substrate, and tantalum material disposed on the alloy layer such that the alloy layer is between the tantalum material and the first major surface of the substrate. The tantalum material includes bonded tantalum particles. The electrical component also includes a dielectric layer disposed on the bonded tantalum particles, a cathode electrode disposed over the tantalum material, and an anode electrode is disposed on the second major surface of the substrate.

In another example, aspects of this disclosure relate to a method that includes disposing an adhesion layer on a first major surface of a substrate, disposing tantalum material including tantalum particles on the adhesion layer, bonding the tantalum particles, and forming an alloy layer. The method further includes disposing a trench through the bonded tantalum particles and the alloy layer, and into the substrate to form a recessed surface within the substrate, and disposing an anode electrode on a second major surface of the substrate.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The techniques of this disclosure generally relate to electrical components and methods for forming such electrical components. In one or more embodiments, the electrical component can include an alloy layer disposed on a substrate, tantalum material including tantalum particles disposed on the alloy layer, a dielectric layer disposed on the tantalum particles, an electrolyte cathode layer disposed on the dielectric layer, and a cathode electrode disposed on the electrolyte cathode layer. An anode electrode can be disposed on the second major surface of the substrate. In one or more embodiments, the electrical component can form a capacitor that can be utilized in any suitable electronic circuit or device.

In general, the present disclosure provides various embodiments of apparatuses, systems, and associated techniques that relate to electrical components. Such electrical components can include any suitable components or circuitry, e.g., capacitors, tantalum capacitors, etc. Tantalum capacitors can be desirable for their reliability and capacitance density. Because of their dimensions, tantalum capacitors are typically disposed on surfaces of integrated circuit boards. At thicknesses greater than 1 mm, typical tantalum capacitors add significantly to the size and thickness of these integrated circuit boards.

One or more embodiments of electrical components described herein can have a thickness, e.g., of no greater than 600 micrometers. Because of this decreased thickness, one or more electrical components described herein can be embedded within an integrated circuit board or integrated into a substrate, thereby enabling smaller electronic packages and assemblies.

Figure 1:
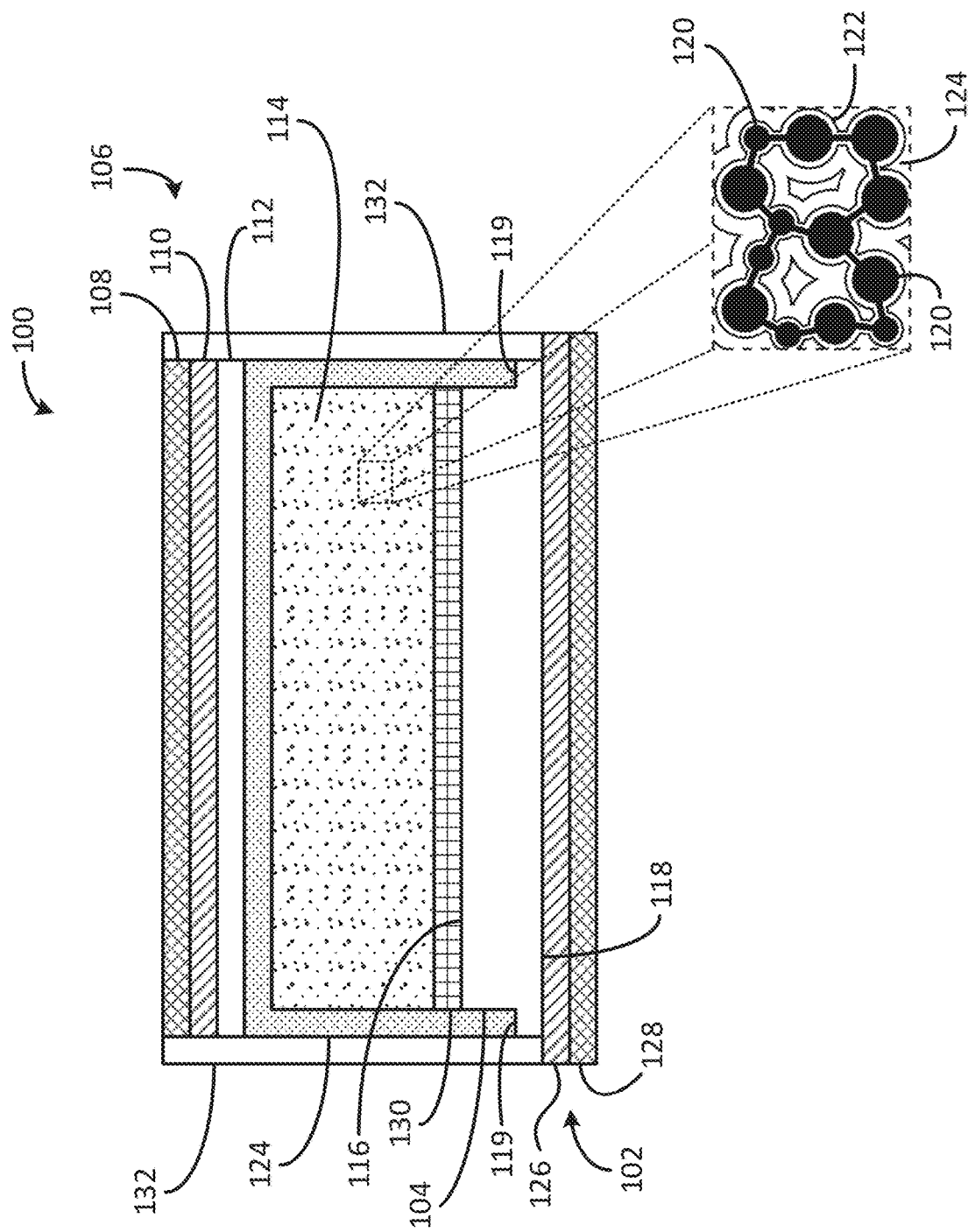
FIG. 1 is a schematic cross-section view of one embodiment of an electrical component.

FIG. 1 is a schematic cross-section view of one embodiment of an electrical component 100. Electrical component 100 includes a substrate 104 having a first major surface 116 and a second major surface 118. The electrical component 100 also includes an alloy layer 130 disposed on the first major surface 116 of the substrate 104. The electrical component 100 further includes tantalum material 114 disposed on the alloy layer 130, where the tantalum material includes tantalum particles 120. Further, the electrical component 100 includes an anode electrode 102 disposed on the second major surface 118 of the substrate 104 and a cathode electrode 106 disposed over the tantalum material 120.

The electrical component 100 can be utilized in any suitable device or electrical circuitry, e.g., printed circuit boards, integrated circuit packages, substrates, glass substrates, ceramic substrates, sapphire substrates, silicon substrates, etc. Further, the electrical component 100 can exhibit any suitable characteristics. For example, the electrical component 100 can include any suitable amount of tantalum by volume of the electrical component. Further, the electrical component 100 can have any suitable dimensions. In one or more embodiments, the electrical component 100 can have a height or thickness as measured in a direction orthogonal to the first and second major surfaces 116, 118 of the substrate 104 of no greater than 500 micrometers.

The substrate 104 can include any suitable material or materials. In one or more embodiments, the substrate 104 includes any suitable conductive material, e.g., tantalum foil, N-type silicon, etc. In one or more examples, the substrate 104 is N-type silicon. As used herein, N-type silicon refers to silicon that has been chemically combined (e.g., doped) with another element or material (e.g., phosphorus) to make the silicon electrically conductive (e.g., resistivity of 200 ohm/centimeter or less). The substrate 104 can include any suitable dimensions and take any suitable shape. In one or more embodiments, the substrate 104 may have a height or thickness extending between the first major surface 116 and the second major surface 118 of at least 50 micrometers and no greater than 300 micrometers. In one or more embodiments, the thickness of the substrate 104 extending between the first major surface 116 and the second major surface 118 may be no greater than 500 micrometers. For example, the thickness of the substrate 104 may be equal to or less than 500 micrometers, equal to or less than 450 micrometers, equal to or less than 400 micrometers, equal to or less than 450 micrometers, equal to or less than 400 micrometers, equal to or less than 350 micrometers, equal to or less than 300 micrometers, equal to or less than 250 micrometers, equal to or less than 200 micrometers, equal to or less than 150 micrometers, or equal to or less than 100 micrometers.

The substrate 104 may take any suitable shape. In one or more embodiments, the substrate 104 includes recessed surfaces 119. The recessed surfaces 119 can be disposed between the first major surface 116 and the second major surface 118. The recessed surfaces 119 can be disposed in the substrate 104 using any suitable technique or techniques, e.g., sawing, cutting, lasering, etc.

Disposed on the first major surface 116 of the substrate 104 is the alloy layer 130. The alloy layer 130 can be disposed using any suitable technique or techniques, e.g., deposition, chemical vapor deposition, physical vapor deposition, sputtering, electroplating, printing, dispensing, sintering, etc. In one or more embodiments, the alloy layer 130 has a thickness of at least 1 micrometer and no greater than 2 micrometers. The alloy layer 130 can include any suitable material or materials, e.g., tantalum, tantalum silicide, tungsten, tungsten silicide, niobium, niobium silicide, etc. In one or more embodiments, the alloy layer 130 includes tantalum silicide. The material of the alloy layer 130 can include a concentration gradient of the material of the substrate 104 at an interface between the alloy layer 130 and the substrate 104. The alloy layer 130 can include a metal silicide, e.g., tantalum silicide, tungsten silicide, niobium silicide, etc. The amount of material of the substrate 104 in the alloy layer 130 may decrease as the distance from the substrate increases such that, at an interface between the alloy layer and the tantalum material 114, the alloy layer does not include any material of the substrate. In other words, at the interface between the alloy layer 130 and the tantalum material 114, the alloy layer includes, e.g., tantalum, tungsten, niobium, etc., but does not include, e.g., silicon.

Disposed on the alloy layer 130 is the tantalum material 114. In one or more embodiments, tantalum material 114 is disposed on the alloy layer 130 such that the alloy layer is between the tantalum material and the substrate 104. Tantalum material 114 includes tantalum particles 120. The tantalum particles 120 may be bonded tantalum particles. Any suitable tantalum particles 120 can be utilized in the tantalum material 114. Further, the tantalum particles 120 can have any suitable dimensions. The tantalum particles 120 can be electrically and mechanically coupled together or bonded using any suitable technique or techniques, e.g., heating, laser, microwave, spark plasma, sintering, etc. Further, the tantalum material 114 can be disposed using any suitable technique or techniques, e.g., deposition, printing, stencil printing, dispensing, jetting, etc. In one or more embodiments, the tantalum material 114 can include tantalum paste. Such tantalum paste can include binding agents to hold the tantalum particles 120 together prior to being bonded. The tantalum paste can include any suitable binding agents, e.g., organic binders, solvents, etc.

The tantalum material 114 can further include a dielectric layer 122 disposed on a surface of one or more of the tantalum particles 120. In one or more embodiments, the dielectric layer 122 can be disposed on surfaces of substantially all of the tantalum particles 120. The dielectric layer 122 can include any suitable dielectric material or materials, e.g., tantalum pentoxide (Ta2O5). Further, the dielectric layer 122 can be formed using any suitable technique or techniques, e.g., anodization, wet-forming, atomic layer deposition, annealing, etc.

Further, the tantalum material 114 can also include an electrolyte cathode layer 124 disposed on the dielectric layer 122. The electrolyte cathode layer 124 can include any suitable material or materials, e.g., manganese dioxide, conductive polymer, etc. Further, the electrolyte cathode layer 124 can include any suitable dimensions and take any suitable shape or shapes. The electrolyte cathode 124 layer can be disposed using any suitable technique or techniques, e.g., pyrolysis, impregnation, printing, dip coating, spin coating, etc. The electrolyte cathode layer 124, in addition to being disposed on the dielectric layer 122 and filling spaces within the tantalum material 114, can extend above the tantalum material. In other words, the electrolyte cathode layer 124 can be disposed between the tantalum material 114 and the cathode electrode 106.

The electrical component 100 can also include the anode electrode 102, which is disposed on the second major surface 118 of the substrate 104. The anode electrode 102 can include any suitable electrically conductive material or materials, e.g., copper, gold, silver, tantalum, graphite, aluminum, chrome, carbon, etc. The anode electrode 102 can also include any suitable dimensions and take any suitable shape or shapes. Further, the anode electrode 102 can be formed using any suitable technique or techniques, e.g., deposition, chemical vapor deposition, physical vapor deposition, sputtering, electroplating, printing, dispensing, etc.

The anode electrode 102 can include one or more layers. In one or more embodiments, the anode electrode 102 can include an anode connector layer 126 disposed on the second major surface 118 of the substrate 104. The anode connector layer 126 can include any suitable dimensions and take any suitable shape or shapes. The anode connector layer 126 can be disposed using any suitable technique or techniques, e.g., deposition, physical vapor deposition (PVD), chemical vapor deposition (CVD), sputtering, electroplating, foil lamination, etc. The anode connector layer 126 may include one or more materials, e.g., copper, gold, silver, aluminum, carbon, or other conductive material.

In one or more embodiments, the anode electrode 102 can also include an anode conductor layer 128 disposed on the anode connector layer 126. The anode conductor layer 128 can also include any suitable dimensions and take any suitable shape or shapes. The anode conductor layer 128 can be formed using any suitable technique or techniques, e.g., deposition, PVD, CVD, sputtering, electroplating, foil lamination, etc. The anode conductor layer 128 can include any suitable electrically conductive material or materials, e.g., copper, gold, silver, aluminum, or other conductive material.

Disposed on the electrolyte cathode layer 124 is the cathode electrode 106. The cathode electrode 106 can include any suitable dimensions and take any suitable shape or shapes. The cathode electrode 106 can include any suitable electrically conductive material or materials, e.g., the same electrically conductive materials described herein regarding the anode electrode 102. The cathode electrode 106 can include one or more layers. Further, the cathode electrode 106 can be formed using any suitable technique, e.g., the same technique or techniques described herein regarding the anode electrode 102.

In one or more embodiments, the cathode electrode 106 can include a cathode connection layer 112 disposed on the electrolyte cathode layer 124 and over the tantalum material 114. The cathode connection layer 112 can include any suitable electrically conductive material or materials, e.g., the same electrically conductive materials described herein regarding the anode electrode 102. Further, the cathode connection layer 112 can include any suitable dimensions and take any suitable shape or shapes. The cathode connection layer 112 can be formed using any suitable technique or techniques, e.g., the same technique or techniques described herein regarding the anode electrode 102.

In one or more embodiments, the cathode electrode 106 can also include a cathode conductor layer 110 disposed on the cathode connection layer 112. The cathode conductor layer 110 can include any suitable electrically conductive material or materials, e.g., the same electrically conductive materials described herein regarding the anode electrode 102. Further, the cathode conductor layer 110 can include any suitable dimensions and take any suitable shape. The cathode conductor layer 110 can be formed using any suitable technique or techniques, e.g., the same technique or techniques described herein regarding the anode electrode 102. In one or more embodiments, the cathode conductor layer 110 can be patterned using any suitable technique or techniques to provide a patterned conductive layer.

In one or more embodiments, the cathode electrode 106 can also include a cathode pad 108 disposed on the cathode conductor layer 110. The cathode pad 108 can include any suitable electrically conductive material or materials, e.g., the same electrically conductive materials described herein regarding the anode electrode 102. Further, the cathode pad 108 can include any suitable dimensions and take any suitable shape. The cathode pad 108 can be formed using any suitable technique or techniques, e.g., the same technique or techniques described herein regarding the anode electrode 102. In one or more embodiments, the cathode pad 108 can be patterned using any suitable technique or techniques to provide a patterned conductive layer.

The electrical component 100 can further include a dielectric 132 disposed on at least one side of the electrical component. The at least one side of the electrical component 100 can be substantially orthogonal to the first major surface 116 of the substrate 104. The dielectric 132 can be disposed such that the electrolyte cathode layer 124 is disposed between the dielectric 132 and the alloy layer 130. The dielectric 132 can be disposed on sides of the substrate 104, the electrolyte cathode layer 124, and the cathode electrode 106. The dielectric 132 can also be disposed on the anode electrode 102. The dielectric 132 can include any suitable dimensions and take any suitable shape or shapes. The dielectric 132 can be disposed using any suitable technique or techniques, e.g., spin coating, screen printing, dispensing, etc. The dielectric 132 may include one or more materials, e.g., polyimide, ceramic, mica, graphite, or other dielectric material.

Figure 2:
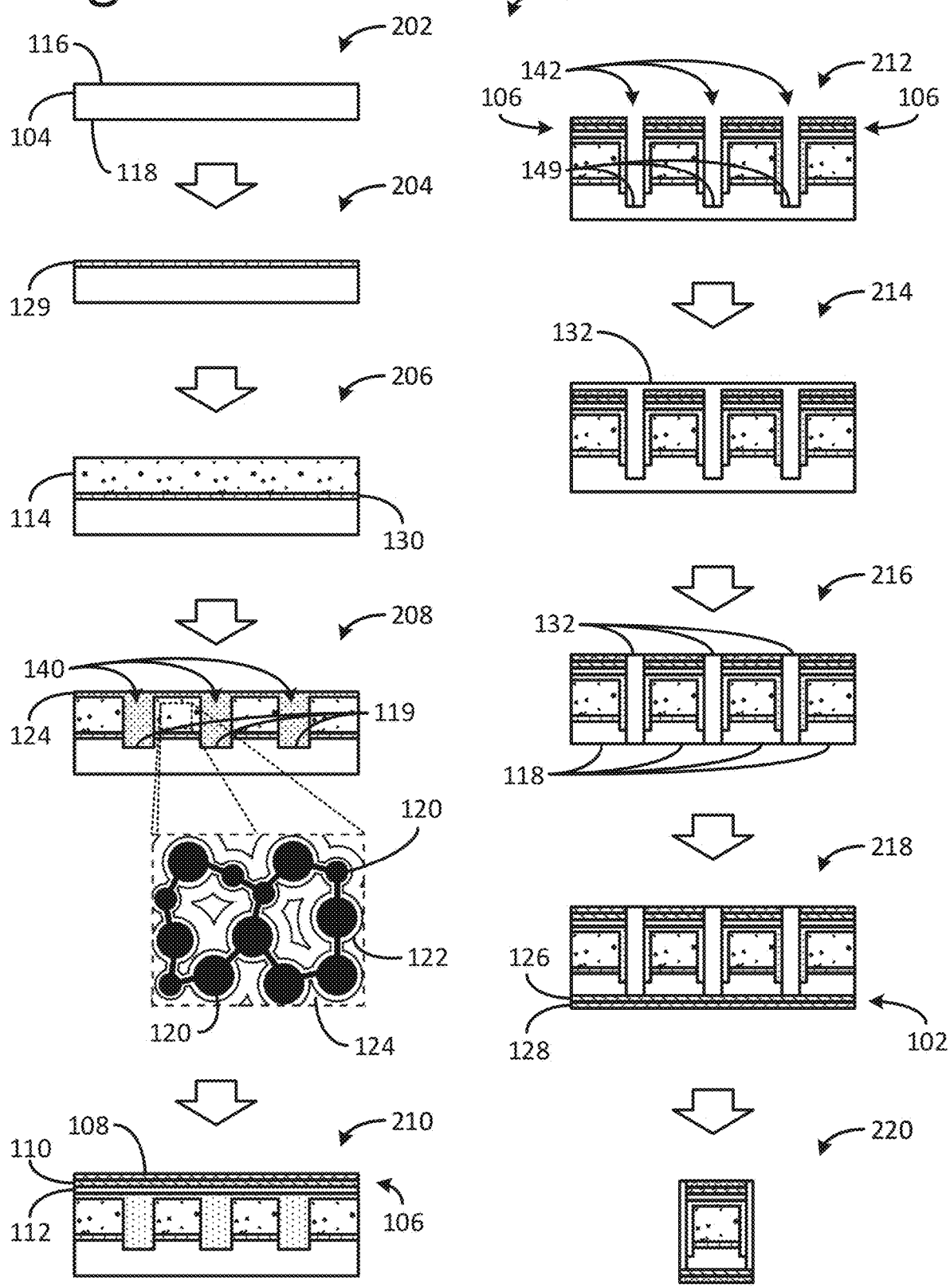
FIG. 2 is a schematic flow diagram of a process for forming the electrical component of FIG. 1.

The electrical component 100 can be manufactured utilizing any suitable technique or techniques. For example, FIG. 2 is a schematic flow diagram of one embodiment of a method 200 of forming a plurality of electrical components 100. Although described in reference to electrical component 100 of FIG. 1, the method 200 can be utilized to form any suitable electrical component.

At 202, The substrate 104 is provided. The substrate 104, includes the first major surface 116 and the second major surface 118 opposite the first major surface.

At 204, an adhesion layer 129 can be disposed on the first major surface 116 of the substrate 104. The adhesion layer 129 may be disposed using any suitable technique or techniques, e.g., deposition, PVD, CVD, sputtering, electroplating, foil lamination, etc. The adhesion layer 129 can include any suitable material or materials, e.g., tungsten, titanium, niobium, etc.

At 206, the tantalum material 114 including tantalum particles 120 can be disposed on the adhesion layer 129 using any suitable technique or techniques. The tantalum material 114 may include, e.g., tantalum powder, a tantalum slug, tantalum paste, etc. In embodiments where the tantalum material 114 includes tantalum powder, a press tool may be used to dispense the tantalum powder and apply force to densify the powder and bond it to the adhesion layer 129. In embodiments where the tantalum material 114 includes tantalum paste, the tantalum paste can be dried and debindered using any suitable technique or techniques at 206, for example, heating the tantalum paste.

In one or more embodiments, the tantalum material 114 can be bonded and the alloy layer 130 can be formed at 206 using any suitable technique or techniques. In one or more embodiments, bonding the tantalum material 114 can include sintering the tantalum material. Bonding the tantalum material 114 can cause the tantalum particles 120 to at least partially fuse together to form one or more mechanical and electrical connections between the tantalum particles. Additionally, bonding can cause one or more of the tantalum particles 114 to fuse to the alloy layer 130, forming at least one mechanical and electrical connection between the tantalum material and the alloy layer. In one or more embodiments, forming the alloy layer 130 includes sintering the adhesion layer 129. Sintering the adhesion layer 129 can cause the adhesion layer to form the alloy layer 130. During formation of the alloy layer 130, a concentration gradient of the material of the substrate 104 can be formed in the alloy layer 130. The concentration gradient can be formed such that the interface between the alloy layer 130 and the substrate 104 includes stochiometric metal silicide (e.g., tantalum silicide, niobium silicide, titanium silicide, etc.), and the interface between the alloy layer and the tantalum material 114 includes metal (e.g., tantalum, niobium, titanium, etc.). The alloy layer 130 can form at least one mechanical and electrical connection with the substrate 104. In one or more embodiments, the tantalum material 114 and the adhesion layer 129 can be sintered by heating the material to a temperature of at least 1200 degrees Celsius and no greater than 3000 degrees Celsius.

At 208, one or more trenches 140 can be disposed through the bonded tantalum particles 120 and the alloy layer 130, and into the substrate 104 to form one or more recessed surfaces 119 in the substrate. The one or more trenches 140 can be disposed using any suitable technique or techniques, e.g., sawing, cutting, lasering, etc.

Further, at 208, the dielectric layer 122 can be disposed on the tantalum particles 120 using any suitable technique or techniques. In one or more embodiments, the dielectric layer 122 may be disposed using, e.g., anodization, wet-forming, atomic layer deposition, annealing, etc. The dielectric layer 122 can include any suitable dielectric material or materials, e.g., tantalum pentoxide.

Still further, at 208, the electrolyte cathode layer 124 can be disposed on the dielectric layer 122 using any suitable technique or techniques. In one or more embodiments, the electrolyte cathode layer 124 may be disposed using, e.g., pyrolysis, impregnation, printing, dispensing, dip-coating, etc. The electrolyte cathode layer 124 can include any suitable material or materials, e.g., manganese dioxide, conductive polymer, etc. In one or more embodiments, the electrolyte cathode layer 124 is disposed over at least a portion of the alloy layer 130 disposed on the first major surface 116. In other words, the electrolyte cathode layer 124, in addition to being disposed on the electrolyte cathode layer 124 and filling spaces within the tantalum material, can be disposed such that the electrolyte cathode layer extends above the tantalum material 114, into the trenches 140, and over one or more sides of the alloy layer 130.

At 210, cathode electrode 106 can be disposed on the electrolyte cathode layer 124 using any suitable technique or techniques, e.g., deposition, PVD, CVD, sputtering, electroplating, foil lamination, etc. In one or more embodiments, disposing the cathode electrode 106 includes disposing the cathode connection layer 112, the cathode conductor layer 110, and the cathode pad 108. The cathode connection layer 112 may be disposed on the electrolyte cathode layer 124 using any suitable technique or techniques, e.g., deposition, PVD, CVD, sputtering, electroplating, foil lamination, etc. The cathode conductor layer 110 may be disposed on the cathode connection layer 112 using any suitable technique or techniques, e.g., deposition, PVD, CVD, sputtering, electroplating, foil lamination, shadow masking, etc. The cathode pad 108 may be disposed on the cathode conductor layer 110 using any suitable technique or techniques, e.g., deposition, PVD, CVD, sputtering, electroplating, foil lamination, shadow masking, etc.

At 212, one or more trenches 142 can be disposed through the cathode electrode 106, the electrolyte cathode layer 124 and the substrate 104 to form one or more recessed surfaces 149 and a plurality of cathode electrodes 106. The one or more trenches 142 can be disposed using any suitable technique or techniques, e.g., sawing, cutting, lasering, etc.

At 214, the dielectric 132 can be disposed in the trenches 142 using any suitable technique or techniques, e.g., spin coating, screen printing, dispensing, deposition, sputtering, dip coating, etc. The dielectric 132 can be disposed on the recessed surfaces 149 and over the cathode electrodes 106. At 216, a portion of the dielectric 132 can be removed. The portion of the dielectric 132 can be removed using any suitable technique or techniques, e.g., plasma etching, wet-etching, dry-etching, lasering, etc. In one or more embodiments, removal of the portion of the dielectric 132 exposes the plurality of cathode electrode pads 108. Additionally, at 216, a portion of the substrate 104 can be removed using any suitable technique or techniques, e.g., grinding, cutting, lasering, sawing, etc. In one or more embodiments, removal of the portion of the substrate 104 can expose the dielectric 132. Such exposed surfaces of the dielectric 132 may be co-planer with the second major surface 118 of the substrate 104.

At 218, the anode electrode 102 can be disposed on the second major surface 118 of the substrate 104 and over the exposed surfaces of the dielectric 132 using any suitable technique or techniques, e.g., deposition, chemical vapor deposition, physical vapor deposition, sputtering, electroplating, printing, dispensing, etc. In one or more embodiments, disposing the anode electrode 102 includes disposing the anode connection layer 126 and the anode conductor layer 128. The anode connection layer 126 may be disposed on the second major surface 118 of the substrate 104 and over the exposed surfaces of the dielectric 132 using any suitable technique or techniques, e.g., deposition, chemical vapor deposition, physical vapor deposition, sputtering, electroplating, printing, dispensing, etc. The anode conductor layer 128 can be disposed on the anode connection layer 126 using any suitable technique or techniques, e.g., deposition, chemical vapor deposition, physical vapor deposition, sputtering, electroplating, printing, dispensing, etc.

At 220, the electronic devices 100 can be singulated. The electronic devices 100 may be singulated using any suitable technique or techniques, e.g., cutting, dicing, sawing, laser cutting, etc. In one or more embodiments, singulating the electronic devices 100 may include removing a portion of the dielectric 132 and the anode electrode 102.

Figure 3:
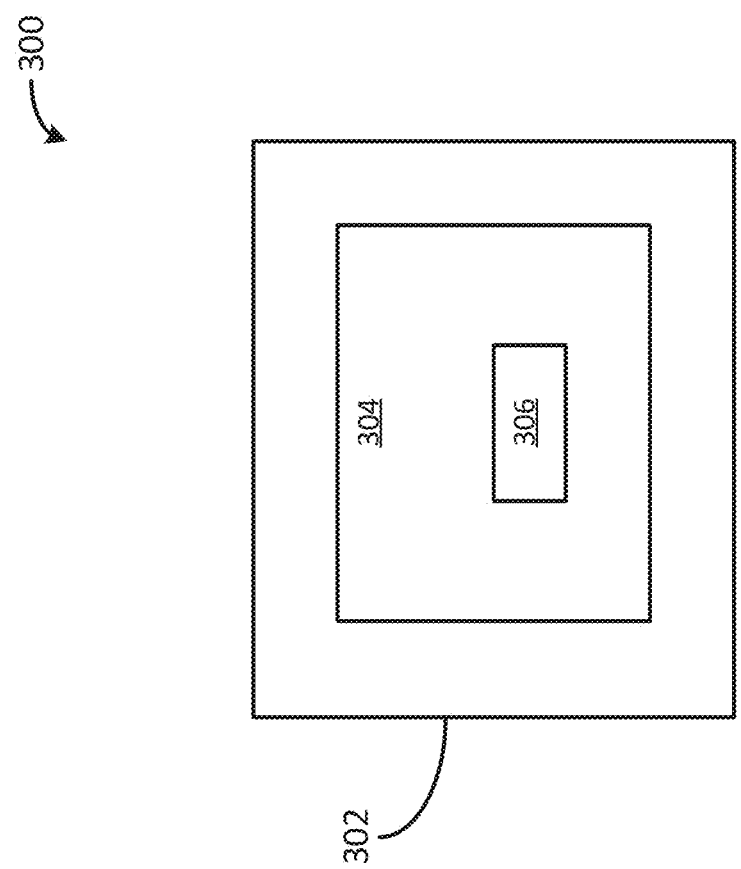
FIG. 3 is a schematic diagram of an implantable medical device including the electrical component of FIG. 1.

The electrical component 100 as described herein can be included in any suitable implantable medical devices. For example, FIG. 3 is a schematic diagram of an implantable medical device 300. Implantable medical device 300 includes a housing 302 and a circuit electronic assembly 304 within the housing. The electronic assembly 304 can include an electrical component 306. The electrical component 306 can include any suitable electrical component, e.g., the electrical component 100 of FIG. 1.

The implantable medical device 300 can include any suitable medical device. In one or more embodiments, the implantable medical device 300 can include an implantable defibrillator, pacemaker, neurostimulator, etc.

It should be understood that various aspects disclosed herein can be combined in different combinations than the combinations specifically presented in the description and accompanying drawings. It should also be understood that, depending on the example, certain acts or events of any of the processes or methods described herein can be performed in a different sequence, can be added, merged, or left out altogether (e.g., all described acts or events can not be necessary to carry out the techniques). In addition, while certain aspects of this disclosure are described as being performed by a single module or unit for purposes of clarity, it should be understood that the techniques of this disclosure can be performed by a combination of units or modules associated with, for example, a medical device.

In one or more examples, the described techniques can be implemented in hardware, software, firmware, or any combination thereof. If implemented in software, the functions can be stored as one or more instructions or code on a computer-readable medium and executed by a hardware-based processing unit. Computer-readable media can include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions can be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein can refer to any of the foregoing structure or any other physical structure suitable for implementation of the described techniques. Also, the techniques could be fully implemented in one or more circuits or logic elements.

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. An electrical component comprising:
   a substrate comprising a first major surface and a second major surface;
   an alloy layer disposed on the first major surface of the substrate;
   tantalum material disposed on and fused to the alloy layer such that the alloy layer is between the tantalum material and the first major surface of the substrate, the tantalum material comprising bonded tantalum particles;
   a dielectric layer disposed on the bonded tantalum particles;
   a cathode electrode disposed over the tantalum material; and
   an anode electrode disposed on the second major surface of the substrate.

2. The electrical component of claim 1, further comprising an electrolyte cathode layer disposed between the tantalum material and the cathode electrode.

3. The electrical component of claim 2, wherein the cathode electrode comprises:
   a cathode connector layer disposed on the electrolyte cathode layer; and
   a cathode conductor layer on the cathode connector layer.

4. The electrical component of claim 2, wherein the electrolyte cathode layer comprises a conductive polymer.

5. The electrical component of claim 1, wherein the dielectric layer comprises tantalum pentoxide ($Ta_2O_5$).

6. The electrical component of claim 1, further comprising a dielectric disposed on at least one side of the electrical component, wherein the at least one side of the electrical component is substantially orthogonal to the first major surface of the substrate.

7. The electrical component of claim 6, wherein an electrolyte cathode layer is disposed between the at least one side of the alloy layer and the dielectric.

8. The electrical component of claim 1, wherein the bonded tantalum particles are sintered together.

9. The electrical component of claim 1, wherein the alloy layer comprises a concentration gradient of the substrate material.

10. The electrical component of claim 1, wherein the anode electrode comprises:
   an anode connector layer disposed on the second major surface of the substrate; and
   an anode conductor layer on the anode connector layer.

11. The electrical component of claim 1, wherein the substrate comprises a doped N-type silicon.

* * * * *